(12) United States Patent
Liu et al.

(10) Patent No.: US 10,020,182 B2
(45) Date of Patent: Jul. 10, 2018

(54) DIGITAL WIRELESS DATA COLLECTION

(71) Applicant: Taiwan Semiconductor Manufacturing Company, Ltd., Hsin-Chu (TW)

(72) Inventors: Hsu-Shui Liu, Pingjhen (TW); Yeh-Chieh Wang, Hsinchu (TW); Jiun-Rong Pai, Jhubei (TW); Pei-Nung Chen, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 867 days.

(21) Appl. No.: 14/216,224

(22) Filed: Mar. 17, 2014

(65) Prior Publication Data
US 2014/0200702 A1    Jul. 17, 2014

Related U.S. Application Data

(63) Continuation-in-part of application No. 12/610,280, filed on Oct. 31, 2009, now Pat. No. 8,676,537.
(Continued)

(51) Int. Cl.
*H01L 21/02*    (2006.01)
*G05B 19/418*   (2006.01)
*G01N 29/14*    (2006.01)
*G01N 29/22*    (2006.01)
*G01N 29/24*    (2006.01)
*G01N 29/44*    (2006.01)
*G01N 29/46*    (2006.01)

(52) U.S. Cl.
CPC .............. *H01L 21/02* (2013.01); *G01N 29/14* (2013.01); *G01N 29/226* (2013.01); *G01N 29/2481* (2013.01); *G01N 29/449* (2013.01); *G01N 29/46* (2013.01); *G05B 19/4189* (2013.01); *G01N 2291/2697* (2013.01)

(58) Field of Classification Search
CPC ................ H01L 21/02; G01N 29/2481; G01N 2291/2697
See application file for complete search history.

(56) References Cited

U.S. PATENT DOCUMENTS 6,952,656 B1 * 10/2005 Cordova .............. G05B 19/042
                                                    700/121
8,676,537 B2 * 3/2014 Liu ........................ G01N 29/14
                                                    700/121
2003/0209097 A1 * 11/2003 Hunter .................... G03F 7/707
                                                    73/865.9

OTHER PUBLICATIONS

Zhang et al., Passive Wireless Monitoring of Wafer Cleanliness During Rinsing of Semiconductor Wafers, Jun. 2010, IEEE Sensors Journal, vol. 10, No. 6, pp. 1048-1055.*

* cited by examiner

*Primary Examiner* — Toan Le
(74) *Attorney, Agent, or Firm* — Haynes and Boone, LLP

(57) ABSTRACT

The present disclosure provides an apparatus for fabricating a semiconductor device. The apparatus includes a portable device. The portable device includes first and second sensors that respectively measure first and second fabrication process parameters. The first fabrication process parameter is different from the second fabrication process parameter. The first and second sensors may communicate the parameters using different and incompatible protocols. The portable device also includes a wireless transceiver that is coupled to the first and second sensors. The wireless transceiver receives the first and second fabrication process parameters and transmits wireless signals containing the first and second fabrication process parameters.

20 Claims, 10 Drawing Sheets

Related U.S. Application Data

(60) Provisional application No. 61/232,225, filed on Aug. 7, 2009.

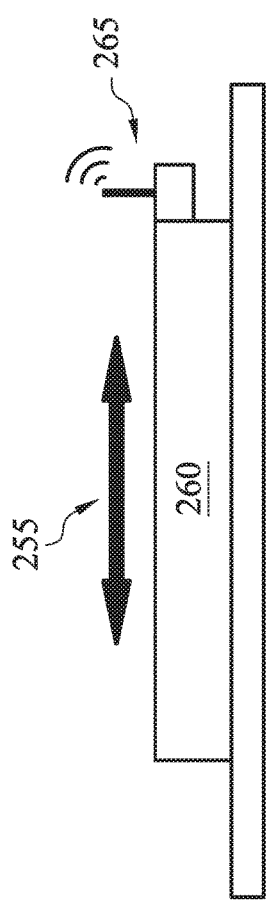
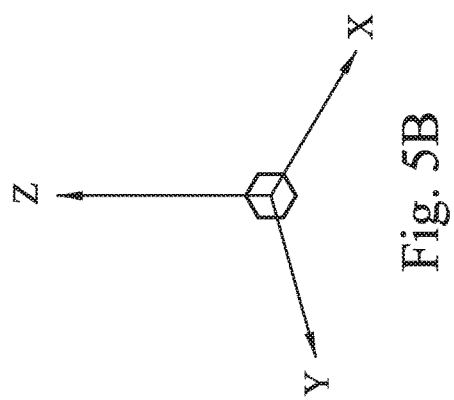

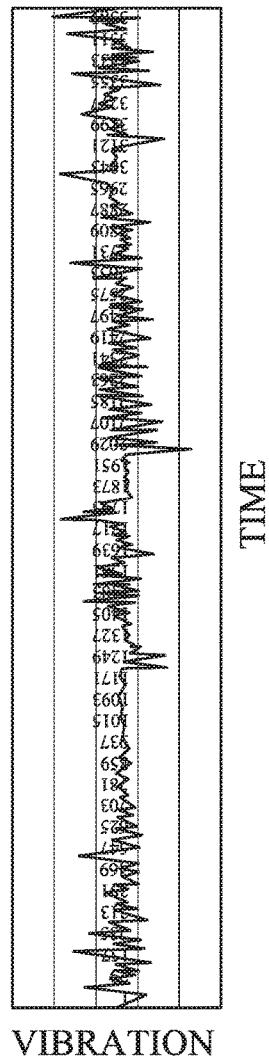

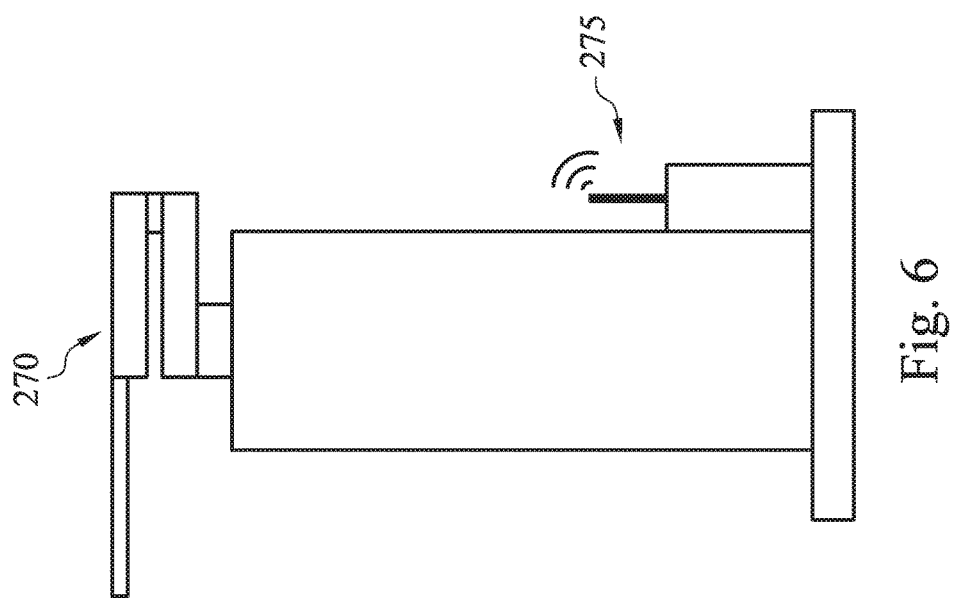

DIGITAL WIRELESS DATA COLLECTION

PRIORITY DATA

This application is a continuation-in-part of U.S. patent application Ser. No. 12/610,280, filed on Oct. 31, 2009, entitled "PORTABLE WIRELESS SENSOR, now issued as U.S. Pat. No. 8,676,537, which claims priority to U.S. Provisional Patent Application Ser. No. 61/232,225, filed on Aug. 7, 2009, entitled "PORTABLE WIRELESS SENSOR," the entire disclosure of each of which is incorporated herein by reference.

TECHNICAL FIELD

The present disclosure relates generally to a sensor, and more particularly, to a portable wireless sensor used in semiconductor fabrication.

BACKGROUND

Semiconductor fabrication requires a plurality of fabrication tools. These fabrication tools use internal or external sensors that measure fabrication process parameters such as temperature, current, voltage, or pressure. However, the parameters that the fabrication tools are capable of measuring are limited by vendor designs, which often do not provide the capability to measure some of the desired key process parameters. In addition, the sensors usually are wired and are difficult to disassemble. Furthermore, the sensors are usually designed to sense only a single parameter, and it is difficult to integrate additional functionalities into the sensors.

Therefore, while existing semiconductor fabrication sensors have been generally adequate for their intended purposes, they have not been entirely satisfactory in every aspect.

SUMMARY

One of the broader forms of the present disclosure involves an apparatus for fabricating a semiconductor device. The apparatus includes a portable device that includes, first and second sensors that measure first and second fabrication process parameters, the first fabrication process parameter being different from the second fabrication process parameter; and a wireless transceiver that is coupled to the first and second sensors, the wireless transceiver receiving the first and second fabrication process parameters and transmitting wireless signals containing the first and second fabrication process parameters.

Another of the broader forms of the present disclosure involves an apparatus for fabricating a semiconductor device. The apparatus includes a portable device that includes, first and second sensors that measure first and second processing data in an analog form; a signal converter that converts the first and second processing data from the analog form into a digital form; a micro-controller that modulates the measured first and second processing data using a predetermined modulation scheme; and a wireless transceiver that transmits wireless signals containing the modulated first and second processing data.

Still another of the broader forms of the present disclosure involves a method of fabricating a semiconductor device. The method includes measuring a first fabrication process parameter using a first sensor; measuring a second fabrication process parameter using a second sensor, the second fabrication process parameter being different from the first fabrication process parameter; and transmitting wireless signals containing the measured first and second fabrication process parameters using a wireless transceiver; and configuring the wireless transceiver and the first and second sensors so that the wireless transceiver and the first and second sensors are integrated into a single portable device.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 5A is a diagrammatic view of another exemplary embodiment and application of the wireless portable multi-function sensor of FIG. 3;

FIG. 5B is a diagrammatic view of a 3-dimensional axes structure illustrating the orientation of the wireless portable multi-function sensor;

FIGS. 5C-5E are exemplary data plots generated by the wireless portable multi-function sensor of FIG. 5A; and FIG. 6 is a diagrammatic view of a further exemplary embodiment and application of the wireless portable multi-function sensor of FIG. 3.

DETAILED DESCRIPTION

Figure 1:
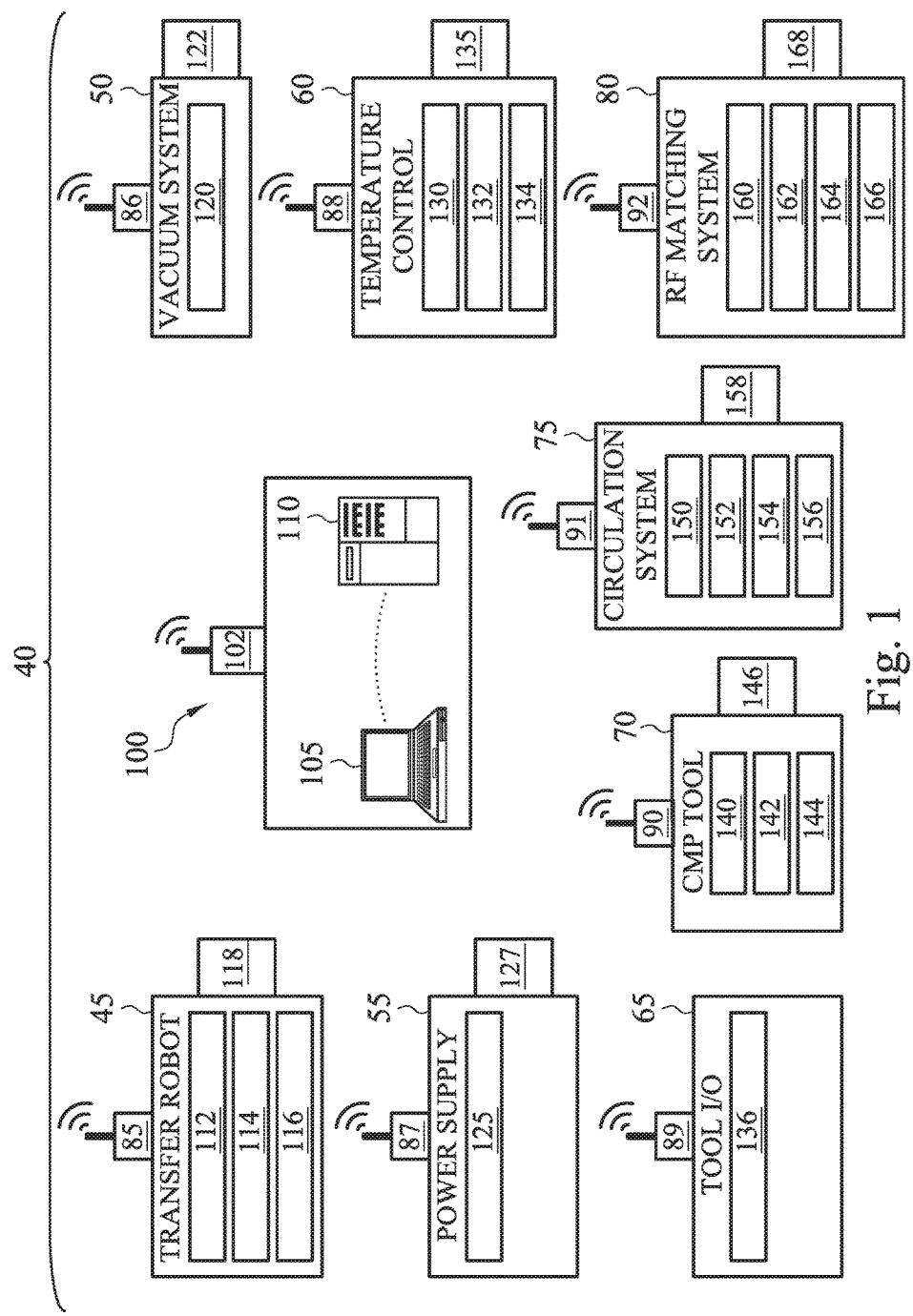
FIG. 1 is a diagrammatic view of a semiconductor fabrication system.

It is understood that the following disclosure provides many different embodiments, or examples, for implementing different features of various embodiments. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Illustrated in FIG. 1 is a diagrammatic view of a semiconductor fabrication system 40. The semiconductor fabrication system 40 includes a plurality of semiconductor fabrication tools. In an embodiment, the semiconductor fabrication system 40 includes a transfer robot 45, a vacuum system 50, a power supply 55, a temperature control 60, an input/output (I/O) tool 65, a chemical-mechanical polishing (CMP) tool 70, a circulation system 75, and a radio frequency (RF) matching system 80. One or more sensors are detachably coupled to each of the fabrication tools 45-80. These sensors are used to collect fabrication data (also known as fabrication process parameters), the details of which will be discussed below. The fabrication tools 45-80 also include wireless transceivers 85, 86, 87, 88, 89, 90, 91, and 92, respectively. The wireless transceivers 85-92 each are a blue-tooth transceiver in the embodiment shown in FIG. 1, but may be transceivers of different technologies in alternative embodiments, such as Wi-Fi or USB. The wireless transceivers 85-92 are each electrically coupled to the respective sensors 112-166 in the respective fabrication tools 45-80, so that the transceivers receive fabrication data collected by the sensors. In an embodiment, the wireless transceivers 85-92 are integrated into the sensors on the respective fabrication tools 45-80.

The semiconductor fabrication system 40 further includes a diagnostic tool 100. The diagnostic tool 100 includes a wireless transceiver 102, a data miner 105, and a centralized server 110. The wireless transceiver 102 is similar to the transceivers 85-92 and is electrically coupled to the data miner 105. The data miner 105 in the present embodiment is a portable computing device, for example a laptop. The data miner 105 is electrically coupled to the centralized server 110, which in the present embodiment is a Computer Integration Manufacturing (CIM) system used for monitoring and controlling semiconductor fabrication processes. In alternative embodiments, the data miner 105 and the centralized server 110 may be implemented as other suitable processing and computing devices and may be integrated as a single unit.

The sensors in each of the fabrication tools 45-80 will now be described in more detail. The transfer robot 45 includes a current sensor 112, a pressure sensor 114, a vibration sensor (also referred to as a motion sensor) 116, and an I/O interface 118. To move objects such as wafers during a fabrication process, the transfer robot 45 uses a motor (not illustrated) that runs on electricity. The current sensor 112 is used to sense the amount of current in the motor. If the sensed current is outside of a predetermined normal range, it indicates a problem with the operation of the motor. For example, if the sensed current is too high, the motor may be overloaded and may be in danger of failing. The transfer robot 45 may also have mechanical "arms" that use a vacuum pipe (not illustrated). The amount of pressure inside the vacuum pipe is monitored by the pressure sensor 114, so that problems with the vacuum pipe such as jams, snaps, or leaks will be detected. The vibration sensor 116 helps gauge the performances and conditions of various components of the transfer robot 45 by sensing the vibration of these components.

The vacuum system 50 controls internal pressures of various types of equipment of a semiconductor fabrication system, such as the fabrication tools of the fabrication system 40. The vacuum system 50 includes pressure sensors 120 (for production chamber and pumping line) and an I/O interface 122. The pressure sensors 120 are used to monitor pumping speed, gas partial pressure, and chamber pressure (if a vacuum chamber is used for the vacuum system 50) of the vacuum system 50. The chamber pressure is correlated to an angle of the valve used to adjust the pressure of the chamber. Thus, tuning the valve angle in turn regulates the pressures of the vacuum system 50. The reading from the pressure sensors 120 allows precise turning of the valve angles. Further, valve angles for multiple chambers can be matched so that the pressures inside these chambers are the same.

The power supply 55 provides electrical power to various types of equipment of a semiconductor fabrication system, such as the fabrication tools of the fabrication system 40. The power supply 55 includes a power sensor 125 and an I/O interface 127. The power sensor 125 monitors and compares the amount of input power ("line-in" power) and amount of output power of the power supply 55. The reduction of power between the input power and the output power is the power loss. If the power loss becomes excessively high, it means some components of the fabrication tool are close to failure.

The temperature control 60 regulates the temperatures of various types of equipment of a semiconductor fabrication system, such as the fabrication tools of the fabrication system 40. The temperature control 60 includes current sensors 130, a resistance sensor 132, temperature sensors 134, and an I/O interface 135. The temperature control 60 uses a heating device (such as a resistance heater, not illustrated) to generate heat and a cooling device (such as a refrigeration compressor, not illustrated) to generate a cooling flow (coolant or de-ionized water). The heating and cooling devices both run on electrical current, and the amount of current in these devices is monitored by the current sensors 130. As discussed above with reference to the other current sensors, the current sensors 130 will detect a problem in the heating and cooling devices based on the amount of current measured. Further, the resistance of the heating device is measured by the resistance sensor 132, which will also help indicate whether a problem exists in the heating device. The temperature sensors 134 include thermocouples that are coupled to the fabrication tool in different internal and external locations. Thus, the temperatures throughout the fabrication tool are obtained. If the measured temperature at a specific location is too high or too low, the temperature setting is adjusted to address this condition.

The I/O tool 65 includes external sensors 136 that are installed on fabrication tools. The external sensors 136 are used to measure desired data (fabrication process parameters) that a given fabrication tool either does not have the capability to measure or lacks a sufficient number of I/O ports for routing. Thus, the external sensors measure these parameters and provide a simulated I/O port to a user. The I/O tool 65 assigns a system variable identification (SVID) to the measured parameters, so that these parameters will be recognized by the fabrication system 40 during later processing. As examples, the external sensors 136 may be flow meters installed on a circulation loop to ensure steady process conditions, or differential pressure manometers installed on exhaust pipes to guarantee appropriate heat loss and flow pattern, or thermocouples installed on a chamber housing/lid/chuck to compare thermo uniformity. In an embodiment, these external sensors 136 may include the sensors 112-134 discussed above as well as the sensors that will be discussed below shortly.

The CMP tool 70 is used to polish and remove surface layer of a wafer. The CMP tool 70 includes vibration sensors 140, a temperature sensor 142, a resistance sensor 144, and an I/O interface 146. The vibration sensors 40 are used to monitor vibrations of various components of the CMP tool 70, the temperature sensor 142 is used to monitor the temperature of a pad surface (used to polish the wafer, not illustrated), and the resistance sensor 144 is used to monitor the resistance of a de-ionized water rinse, so that the CMP process is ensured to progress smoothly. The CMP tool 70 will be discussed in more detail later as an example of the fabrication tools.

The circulation system 75 is used to perform various chemical processes in semiconductor fabrication, such as etching that is carried out in an etching tank (not illustrated) having an etching solution. The circulation system 75 includes a flow rate sensor 150, a temperature sensor 152, a radiation sensor 154, a level sensor 156, and an I/O interface 158. The flow rate sensor 150 and the temperature sensor 152 are used to monitor the flow rate and the temperature of the etching solution, respectively. The concentration (also referred to as consistency) of the etching solution is correlated to a spectrum of radiation (such as light) that is associated with the etching solution. The spectrum of radiation can be detected by the radiation sensor 154, which may be implemented as a charge-coupled device (CCD). The amount (or level) of etching solution in the etching tank is monitored by the level sensor 156. The sensors 150-156 provide analog outputs, so that the flow rate, the temperature, the concentration, and the level of the etching solution are fine-tuned by the respective sensors 150-156.

The RF/matching system 80 includes an RF power system and a matching system. The matching system is used to match input and output impedances in high frequency operation to minimize power loss and improve efficiency. The matching system includes an RF matching network (not illustrated). The RF power system has a plurality of electronic components, such as resistors, capacitors, inductors, transformers, as well as one or more stages of amplifiers. The RF/matching system 80 includes a power sensor 160, a current sensor 162, a temperature sensor 164, an position sensor 166, and an I/O interface 168. The power sensor 160 is used to monitor the input and output powers of the RF matching system 80 to detect potential failures associated with abnormal power loss. The current sensor 162 is used to monitor the current of different stages of amplifiers to determine if the loading of the amplifier is appropriate. The temperature sensor 164 is used to monitor the temperature of the transformers, which has an inverse correlation with its efficiency. The position sensor 166 of the matching system includes a potentiometer (a variable resistor) that is used to cause voltage variations that lead to changes in capacitance and inductance of the RF matching network, which in effect tunes the RF matching network to a desired state. Since capacitance and inductance together define impedance, it can be said that a specific setting of the potentiometer corresponds to a respective impedance of the RF matching network, and thus the impedance sensor 166 monitors the impedance of the RF matching system 80.

The fabrication tools 45-80 may be collectively referred to as a measurement system. The I/O interfaces 118, 122, 127, 135, 146, 158, and 168 of their respective fabrication tools 45-80 are the default I/O interfaces that the respective fabrication tool is equipped with, and the I/O interfaces either do not have the capability to measure the process parameters that the respective sensors of the respective fabrication tools are operable to measure, or that the I/O interfaces do not provide a sufficient number of I/O ports to supply these respective data to external devices. These shortcomings of the I/O interfaces 118, 122, 127, 135, 146, 158, and 168 represent a disadvantage for fabrication tools not equipped with the respective sensors discussed above. However, for the fabrication tools 45-80 discussed above, no such disadvantage exists since these fabrication tools can gather the desired data through their respective sensors.

After the desired fabrication data are gathered by the appropriate sensors, the wireless transceivers 85-92 of the respective fabrication tools 45-80 send the gathered fabrication data across a wireless interface to the diagnostic tool 100. The fabrication data are received by the wireless transceiver 102, which then routes the data to the data miner 105. The data miner 105 then sends the data to the centralized server 110 for detailed processing and analysis. Thereafter, the centralized server 110 makes a determination as to whether the fabrication data fall within an acceptable range. If not, the centralized server 110 may instruct the data miner 105 to send out a signal via the transceiver 102 to tell the appropriate fabrication tool to make adjustments.

Figure 2:
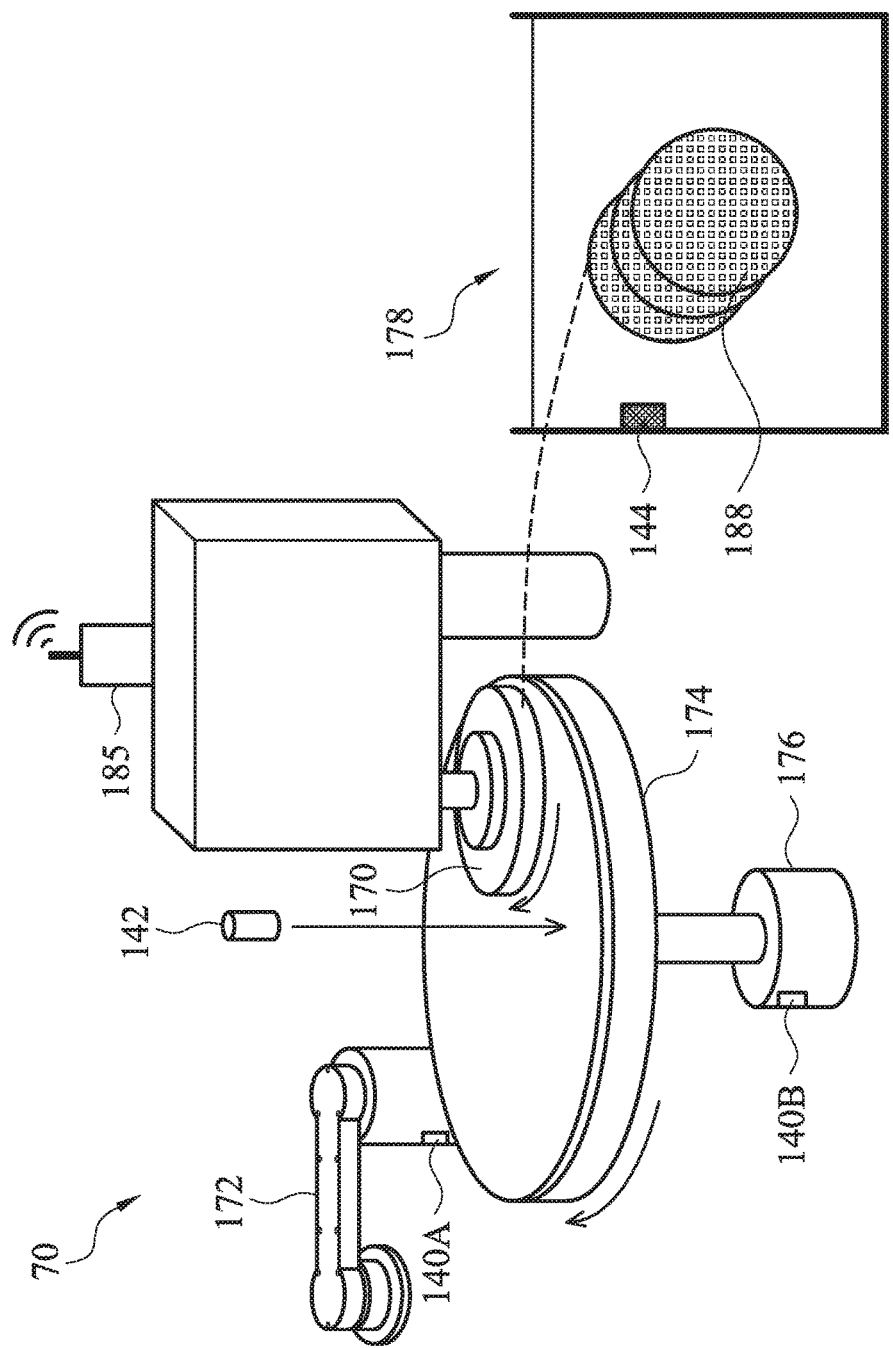
FIG. 2 is a diagrammatic view of an exemplary embodiment of a portion of the semiconductor fabrication system of FIG. 1.

Referring now to FIG. 2, the CMP tool 70 is discussed in more detail so as to provide an example of the operation of the semiconductor fabrication system 40. FIG. 2 illustrates a diagrammatic view of the CMP tool 70 of FIG. 1. The CMP tool 70 includes a polishing head 170, a pad conditioner head 172, a platen 174, a platen gear box 176, a water tank 178 filled with de-ionized water, the sensors 140A-B, 142, and 144 (discussed above with reference to FIG. 1), and a wireless transceiver 185. A semiconductor wafer is secured by the polishing head 170, and the surface of the wafer is polished by the platen 174 as the polishing head 170 moves the wafer across the platen. After polishing, one or more semiconductor wafers 188 are then placed into the water tank 178 to be rinsed with de-ionized water.

The sensor 142 is an infrared radiation detector that is positioned above the platen 174. In an embodiment, the sensor 142 is mounted on the ceiling of a chamber (not illustrated) of the CMP tool 70. The sensor 142 monitors the temperature of the surface of the platen 174 to make sure that the platen is not overheated. Overheating of the surface of the platen 174 indicates high likelihood of failure of the CMP tool 70. The sensors 140A and 140B are vibration sensors implemented as accelerometers and are respectively coupled to the pad conditioner head 172 and the platen gear box 176. The sensors 140A-B monitor the amount of vibration in the CMP tool 70. Excessive vibration also indicates high likelihood of failure of the CMP tool 70. The sensor 144 is a resistance sensor that is coupled to the water tank 178 so as to monitor the resistance of the de-ionized water in the tank. Abnormal resistance variations indicate that the de-ionized water in the water tank 178 is stained by CMP slurry, meaning the de-ionized water has been polluted and needs to be changed.

The heat data, vibration data, and resistance data are respectively gathered by the sensor 142, sensors 140A-B, and the sensor 144, and are thereafter sent to the wireless transceiver 185, which is a Bluetooth transceiver coupled to a suitable portion of the CMP tool 70. The wireless transceiver 185 sends the gathered data wirelessly to the diagnostic tool 100 (FIG. 1) for processing and analysis by the centralized server 110, which is the CIM system of a semiconductor foundry. Depending on the analysis results, the centralized server 110 sends signals back to the CMP tool 70 through the wireless transceivers 102 (FIG. 1) and 185. The CMP tool 70 then adjusts the CMP process accordingly.

In an alternative embodiment for the CMP tool 70 discussed above, each of the sensors 142-144 may have wireless transceivers integrated within, so that each of the sensors 142-144 is capable of wirelessly transferring fabrication data to the diagnostic tool 100 (FIG. 1), as opposed to having to route fabrication data to the standalone wireless transceiver 185 first.

Figure 3:
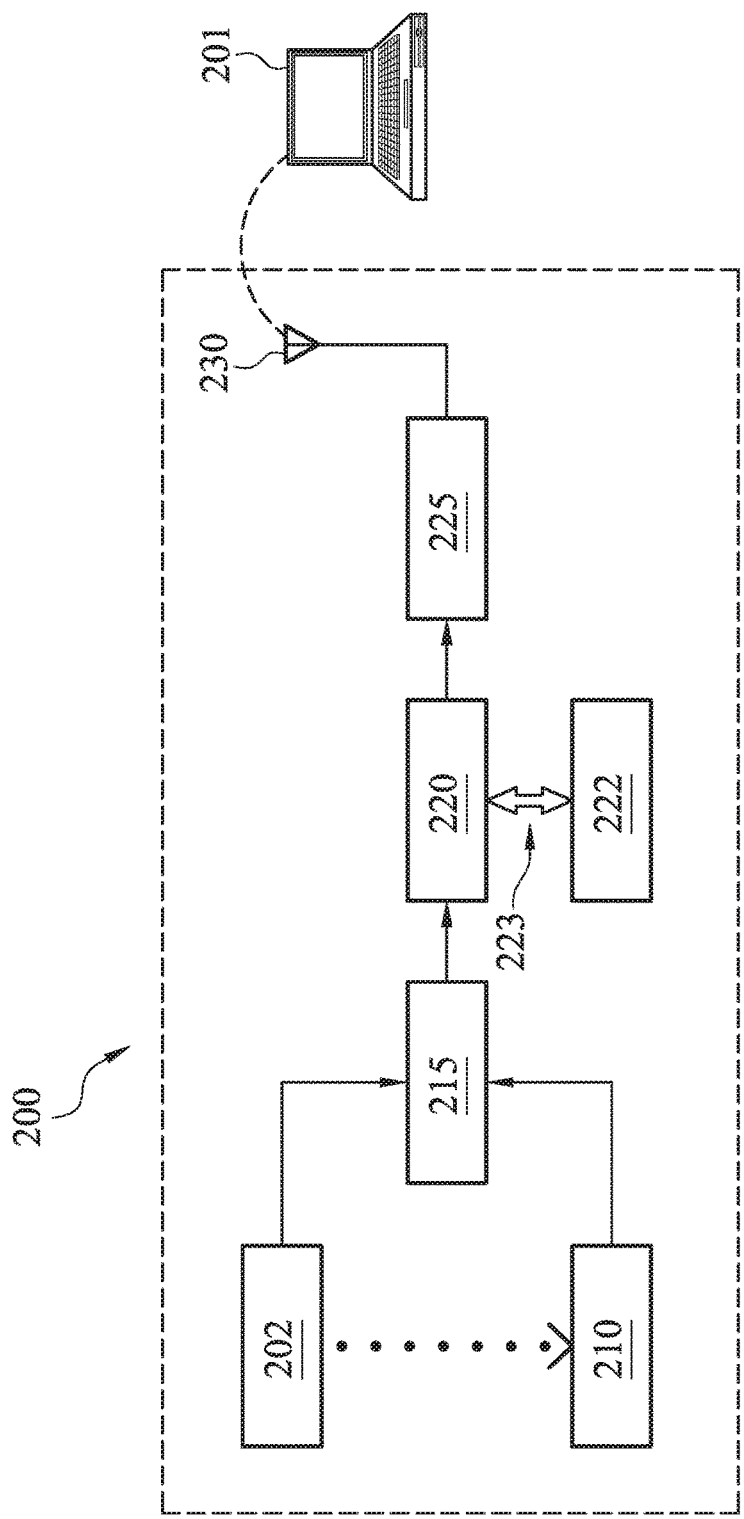
FIG. 3 is a diagrammatic view of a wireless portable multi-function sensor and a diagnostic tool that is wirelessly coupled to the sensor.

FIG. 3 is a diagrammatic view of a wireless portable multi-function sensor (WPMF sensor) 200 and a diagnostic tool 201. The WPMF sensor 200 can be used in place of, or in conjunction with, the wireless transceivers 85-92 and the sensors 112-166 of FIG. 1. In the present embodiment, the WPMF sensor 200 is detachably coupled to a fabrication tool (for example, one of the fabrication tools 45-80 of FIG. 1) to gather fabrication data associated with that tool.

The WPMF sensor 200 includes a plurality of sensors 202 to 210, a signal converter 215, a micro-controller unit (MCU, also referred to as a micro-processor) 220, a storage device 222, a communication interface 223 between the MCU 220 and the storage device 222, and a transceiver 225 that has an optional antenna 230. The sensors 202-210 are similar to the sensors 112-166 discussed above with reference to the FIG. 1 and are used to monitor fabrication data (process parameters) such as voltage, current, resistance, vibration, temperature, etc. The sensors 202-210 output the sensed fabrication data as analog signals. Any number of sensors 202-210 may be implemented in the WPMF sensor 200 depending on design requirements and manufacturing constraints. In alternative embodiments, the sensors 202-210 may be implemented external to the WPMF sensor 200, in which case the WPMF sensor 200 may include ports that are coupled to the external sensors 202-210.

Referring back to FIG. 3, the signal converter 215 receives the output of the WPMF sensors 202-210 as inputs. The signal converter 215 includes a multi-channel analog-to-digital converter in the present embodiment, each channel capable of converting the analog signal output from one of the sensors 202-210 into digital form. In alternative embodiments where the sensors 202-210 output digital signals, the signal converter 215 may perform necessary data processing on the digital signal outputs of the sensors 202-210. The signal converter 215 then outputs the fabrication data to an input of the MCU 220, which performs further processing on the data. In an embodiment, the MCU 220 controls operations of the signal converter 215 and the transceiver 225. In another embodiment, the MCU 220 modulates the data in accordance with a predetermined modulation scheme, such as quadrature phase shift keying (QPSK), quadrature amplitude modulation (QAM), Gaussian frequency shift keying (GFSK), or orthogonal frequency division multiplexing (OFDM). In yet another embodiment, the signal converter 215 is integrated into the MCU 220.

The interface 223 allows the MCU 220 to communicate with the storage device 222. As an example, fabrication data can be transferred between the storage device 222 and the MCU 220 through the interface 223 to enhance the functionalities of the MCU 220. In the present embodiment, the storage device 222 is a secure digital (SD) card, and the interface 223 is an USB port. In alternative embodiments, the storage device 222 may be other forms of memory, including Flash, Memory Stick, Micro-SD, or a hard disk, and the interface 223 may be a serial port, parallel port, FireWire port, or USB port. In yet another alternative embodiment, the storage device 222 may be integrated into the MCU 220.

Referring back to FIG. 3, the fabrication data is sent from an output of the MCU 220 to an input of the transceiver 225 to be broadcast. The transceiver 225 includes a Bluetooth transceiver in the present embodiment. In alternative embodiments, the transceiver 225 may be Wi-Fi or Universal Asynchronous Receiver Transmitter (UART). The antenna 230 is a standalone antenna but may be integrated into the transceiver 225 in alternative embodiments. In further embodiments, the transceiver 225 is integrated into the MCU 220, so that the MCU 220 communicates directly with external devices. In yet another embodiment, the MCU 220 communicates with external devices through the interface 223, or through another suitable interface that is not illustrated. The transmitted fabrication data is received and analyzed by the diagnostic device 201. The diagnostic device 201 includes a laptop computer that has an integrated wireless transceiver (not illustrated) such as a Wi-Fi or a Bluetooth transceiver. Alternatively, the transmitted fabrication data may be received and analyzed by the diagnostic tool 100 of FIG. 1, using the centralized server 110.

The WPMF sensor 200 is portable and can be configured to adapt to a variety of manufacturing and communication platforms. The multiple sensors integrated within the WPMF sensor 200 allow different types of fabrication data to be collected simultaneously. Based on the simultaneously collected fabrication data, a user may then perform a quick analysis using the diagnostic device 201. If the results of the analysis indicate potential problems with the fabrication tool from which the WPMF sensor 200 gathered data, the fabrication tool can be immediately adjusted to prevent manufacturing failures. The adjustment may be made by either a human user or through a computerized feedback control loop.

Figure 4:
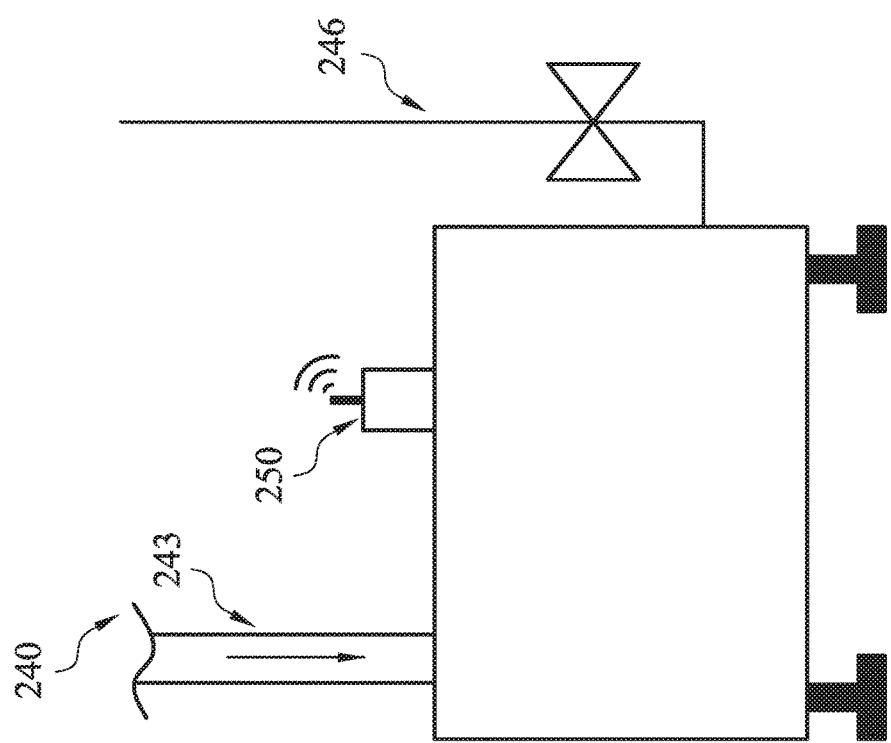
FIG. 4 is a diagrammatic view of an exemplary embodiment and application of the wireless portable multi-function sensor of FIG. 3.

Referring now to FIG. 4, an exemplary embodiment and application of the WPMF sensor 200 is discussed. FIG. 4 illustrates a diagrammatic view of a vacuum pump 240. The vacuum pump 240 includes a process pumping line (inlet) 243, an exhaust pipe (outlet) 246, and a WPMF sensor 250. The vacuum pump 240 is a dry pump in the present embodiment. The vacuum pump 240 may be a cryo-pump in alternative embodiments. Referring back to FIG. 4, the vacuum pump 240 also includes a plurality of internal sensors (not illustrated), including a current sensor that measures motor current (to monitor pump loading), a pressure sensor that measures outlet pressure (to monitor obstruction of the exhaust pipe 246), and a temperature sensor that measures internal pump temperature (to monitor the working temperature of the pump 240).

The WPMF sensor 250 is an exemplary embodiment of the WPMF sensor 200 discussed above with reference to the FIG. 3. The WPMF sensor 250 is placed on an external surface of the vacuum pump 240 and includes a vibration sensor (not illustrated) and a temperature sensor (not illustrated). The vibration sensor is implemented as an accelerometer, and the temperature sensor is implemented as an infrared radiation detector. The vibration sensor monitors the amount of vibration on the vacuum pump 240 during the pump's operation, and the temperature sensor monitors the temperature of the vacuum pump 240 during the pump's operation. When either the vibration or the temperature data is outside an acceptable range but the other parameter is within an acceptable range, action need not necessarily be taken, because the fact that only one process parameter deviates from the normal ranges does not carry much significance. However, when both the vibration and the temperature data are outside the acceptable range, it indicates the vacuum pump 240 is likely to fail soon. Thus, the vacuum pump 240 may be repaired or replaced before actual failure occurs. It is understood that a user may use a laptop to obtain the vibration and temperature data from the vacuum pump wirelessly through the WPMF sensor 250.

The user need not perform actual measurements on the vacuum pump 240, since the measurements are automatically made.

Referring now to FIGS. 5A-5E, another exemplary embodiment and application of the WPMF sensor 200 is discussed. FIG. 5A illustrates a diagrammatic view of an exposure process tool 255. The exposure process tool 255 is used during a photolithography process that forms image patterns on a semiconductor wafer. The exposure process tool 255 includes a moving stage 260 and a WPMF sensor 265. The WPMF sensor 265 is attached to either side of the moving stage 260. In an alternative embodiment, the WPMF 265 is placed over the top surface of the moving stage 260.

Referring back to FIG. 5A, vibrations in the exposure process tool 255 can be caused by defects in various moving components of the exposure process tool 255, including the motor, gear, guider, screw, or bearing (none of which are illustrated). Current fabrication technologies do not provide a measurement of the vibration of the exposure process tool 255. Nonetheless, a relatively small amount of vibration may lead to poor wafer pattern image quality. Further, if the moving stage 260 is not level, the wafers will also have poor pattern image quality. If the wafers having poor pattern image quality are not caught in time, and the wafers undergo etching, they may be unsalvageable and have to be scrapped.

In the present embodiment, the WPMF sensor 265 includes a vibration sensor (not illustrated) and a leveling sensor (not illustrated). The vibration sensor is used to monitor the vibration of the exposure process tool 255, and the leveling sensor is used to monitor the levelness of the moving stage 260, so as to ensure adequate pattern image quality. In the present embodiment, both the vibration sensor and the leveling sensor are implemented as 3-axis microelectromechanical system (MEMS) accelerometers. The MEMS accelerometer has a relatively high sensitivity to gravity. The sensitivity to gravity is utilized to measure the levelness of the accelerometer (and thus the levelness of the moving stage 260), as discussed below.

Referring now to FIG. 5B, the orientation of the accelerometer inside the WPMF 265 can be illustrated by the 3-dimensional axes diagram that has an X-axis, a Y-axis, and a Z-axis. The X, Y and Z axes are substantially orthogonal (perpendicular) to one another. The vibrations along each axis are then measured as audio-like signals. Exemplary illustrations of these audio-like signals are shown in FIGS. 5C, 5D, and 5E, where the vertical axis represents vibration signals measured by the accelerometer, and the horizontal axis represents different points in time. FIG. 5C shows vibration signals measured along the X-axis with respect to time, FIG. 5D shows vibration signals measured along the Y-axis with respect to time, and FIG. 5E shows vibration signals measured along the Z-axis with respect to time. Thereafter, data averaging is performed on the measured vibration signals to ensure a more stable reading of the accelerometer. A low pass filter is then used to filter out the high frequency components of the vibration signals, and the remaining portions of the vibration signals are the leveling signals (not illustrated). To view the leveling signals across a frequency spectrum, a fast Fourier transform (FFT) is performed on the vibration signals.

When the accelerometer is substantially level, the leveling signals with respect to the X-axis and the Y-axis should be very close to 0, while the leveling signal with respect to the Z-axis should be 1 times gravity (represented by g). When the accelerometer is tilted (not level), the leveling signals with respect to the X and Y-axes deviate from 0, and the leveling signal with respect to the Z-axis deviates from g. The leveling signals are analyzed (for example, by the diagnostic tool 201 of FIG. 3) so as to indicate how the accelerometer is tilted. As discussed above, the tilt of the accelerometer is indicative of how the WPMF sensor 265 is tilted and therefore how the moving stage 260 is tilted. The moving stage 260 is then adjusted either through a computerized feedback control loop or by a human user, in a manner so that the accelerometer is more level.

It is understood that with respect to its application for the exposure process tool 255, the wireless aspect of the WPMF sensor 265 offers another advantage (it being understood that different advantages are offered by different embodiments): the vibration data would have been unintentionally affected by the cables or wires of a traditional wired sensor, whereas no such cables or wires exist to cause vibration interference in the present embodiment as the WPMF sensor 265 functions wirelessly.

Referring now to FIG. 6, a further exemplary embodiment and application of the WPMF sensor 200 is discussed. FIG. 6 is a diagrammatic view of a transfer robot 270 that is similar to the transfer robot 45, and on which a WPMF sensor 275 is mounted. The WPMF sensor 275 includes a current sensor, a voltage sensor, and a vibration sensor (none of which are illustrated). The current sensor is used to monitor the current load of a motor (not illustrated) of the transfer robot 270. To control the operation of the motor, digital control signals have to be transformed into analog signals using an encoder (not illustrated). The voltage sensor of the WPMF 275 is used to monitor the voltage of the encoder, so that a phase character can be calculated if the motor is a servo motor, or that a step loss can be calculated if the motor is a stepping motor. The vibration sensor is implemented as an accelerometer and is used to monitor the vibrations of various components of the transfer robot 270 so as to gauge the conditions and performance of these components. Thus, the WPMF 275 gathers fabrication data with respect to motor current, encoder voltage, and transfer robot component vibrations. These gathered fabrication data are wirelessly sent to the diagnostic tool 201 (FIG. 3), either individually or collectively, to determine the quality of the transfer robot 270 and whether it needs to be repaired or overhauled.

Figure 7:
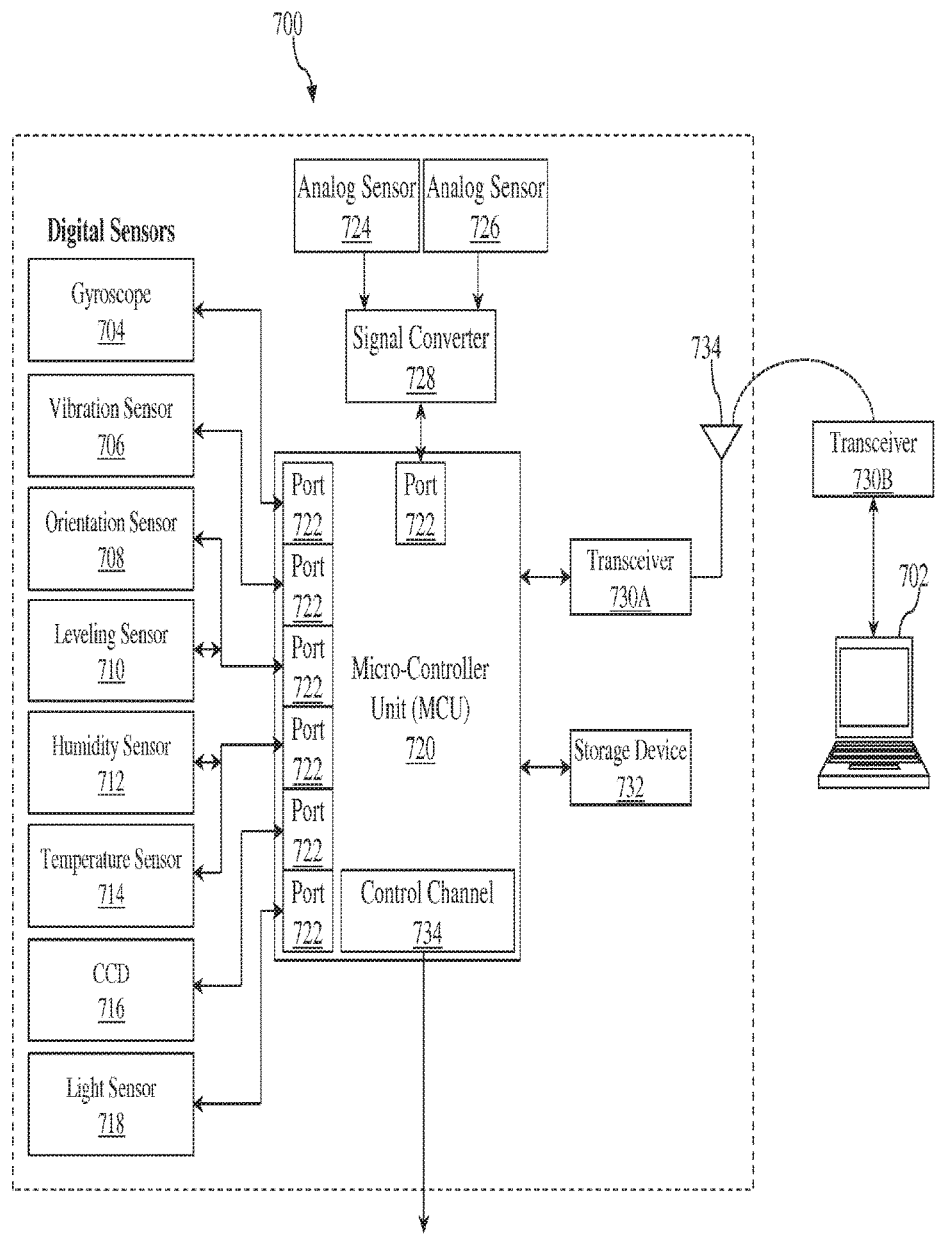
FIG. 7 is a diagrammatic view of a wireless sensing system and a wirelessly coupled diagnostic tool according to aspects of the present disclosure.

In further embodiments, a wireless sensing system is provided that gathers data from additional types of sensing devices. FIG. 7 is a diagrammatic view of one such wireless sensing system 700 and a wirelessly coupled diagnostic system 702 according to aspects of the present disclosure. In particular, the illustrated wireless sensing system 700 includes a number of advanced digital sensors that provide precise measurements of fabrication parameters and, by virtue of signal processing within the sensor, may offer greater precision, customization, and flexibility. As the wireless sensing system 700 may be detachably coupled to a fabrication tool, in various embodiments, the wireless sensing system 700 includes a plurality of sensors 704-718 selected based on the fabrication tool and the fabrication parameters to be measured. By flexibly adapting to the fabrication environment, the wireless sensing system 700 is suitable for use with a wide range of fabrication processes. As merely some examples, the system 700 may be used in place of, or in conjunction with, the wireless transceivers 85-92 and the sensors 112-166 of FIG. 1. In various embodiments, wireless sensing systems 700 are detachably coupled to fabrication tools including fabrication tools 45-80 of FIG. 1 in order to gather fabrication data associated with the respective tool.

In the illustrated embodiments, the wireless sensing system 700 is detachably coupled to a wafer-transporting container such as a front-opening universal pod (FOUP). FOUPs are used to store and transport semiconductor wafers between fabrication tools, and an exemplary FOUP is described in more detail in the context of FIG. 8. In such applications, sensors may be selected to monitor the motion of the FOUP, the docking of the FOUP in a load port, the atmosphere with the FOUP, and other relevant parameters. The illustrated sensors 704-718 include a gyroscope 704, a vibration sensor 706, an orientation sensor 708 (i.e., a compass), a leveling sensor 710, a humidity sensor 712, a temperature sensor 714, a CCD (Charge-Coupled Device) sensor 716, and a light sensor 718, although it is understood that these are merely examples of suitable sensors. Other embodiments of the wireless sensing system 700 include other sensors not illustrated here.

The sensors 704-718 are communicatively coupled to interface ports 722 of a micro-controller unit (MCU) 720. The MCU 720 receives and aggregates sensor data from the sensors 704-718 via these ports 722. Because the exemplary sensors 704-718 report sensor data in a digital format, the ports of the MCU 720 communicate with the sensors 704-718 according to a digital protocol. Examples of digital protocols used by the sensors 704-718 to transmit digital sensor data include UART (Universal Asynchronous Receiver and Transmitter), TCP/IP, USB, I$^2$C, and other digital protocols. In some embodiments, the MCU 720 includes multi-protocol ports 722 that determine a preferred protocol of an attached sensor and communicate accordingly. Multi-protocol ports 722 allow the MCU 720 to be used and reused with a wide variety of sensor configurations, but may add to the expense and bulk of the MCU 720. Accordingly, in some embodiments, one or more ports 722 of the MCU 720 support only a single protocol for communicating with a sensor. In further embodiments, the MCU 720 includes at least one single-protocol port 722 and at least one multi-protocol port 722. In contrast to some analog protocols, in many digital protocols, the MCU 720 requests sensor data from a sensor and acknowledges when sensor data has been received. The MCU 720 may also send various configuration instructions to the sensors. Thus, the ports 722 may be bi-directional and capable of transmitting data acquisition signals and control signals from the MCU 720 to the sensors 704-718.

One advantage of digital communications between the sensors 704-718 and the MCU 720 is that, in some embodiments, multiple sensors share a single port 722. In the illustrated embodiment, the orientation sensor 708 and the leveling sensor 710 communicate via the same port 722 and the humidity sensor 712 and the temperature sensor 714 communicate via the same port 722. (The selection of sensors to share a port is merely arbitrary.) The physical connections used to couple multiple sensors to a single port 722 are often determined in part by the protocols used by the sensors, and may include bus, ring, star, and/or daisy-chain topologies. Likewise, the techniques for obtaining sensor data from multiple sensors using a single port 722 are often determined in part by the protocol or protocols. In some embodiments, sensors that share a port 722 utilize a common protocol or compatible protocols configured to share resources. In some such embodiments, the common protocol allows for concurrent and/or sequential transmission of sensor data by the sensors. However, in other embodiments, sensors using different, incompatible protocols may be connected to a single multi-protocol port 722. In one embodiment using a time-division technique, the port 722 requests data from a first sensor during a first time interval according to the first sensor's protocol, and after the first sensor has reported the sensor data, the port 722 requests data from a second sensor during a second time interval according to the second sensor's particular protocol. This allows for protocol-independent port sharing.

The MCU 720 may also receive sensor data from one or more analog sensors 724 and 726. Accordingly, in some embodiments, the wireless sensing system 700 includes a signal converter 728 substantially similar to signal converter 215 of FIG. 3. In that regard, the signal converter 728 may include a multi-channel analog-to-digital converter, each channel capable of converting the analog signal output from one of the analog sensors 724 and 726 into a digital form. The signal converter 728 may also perform additional signal conditioning such as amplification, filtering, and/or aggregation of the analog data signals of the analog sensors 724 and 726 before digitizing, after digitizing, or both. The signal converter 728 may then output the sensor data to the MCU 720.

Once the MCU 720 has obtained sensor data from the digital sensors 704-718 and/or the analog sensors 724 and 726, it may format the sensor data for transmission by the transceiver 730A. In many embodiments, the MCU 720 tags sensor data with an ID tag corresponding to the sensor that produced it. This allows the recipient (e.g., the diagnostic system 702) to recognize the type of data being received and to correlate the sensor data with the sensor that produced it. The MCU may also modulate the sensor data in accordance with a predetermined modulation scheme prior to providing the data to the transceiver 730A. Suitable modulation schemes include quadrature phase shift keying (QPSK), quadrature amplitude modulation (QAM), Gaussian frequency shift keying (GFSK), and/or orthogonal frequency division multiplexing (OFDM). The MCU 720 may also store the sensor data to a storage device 732 such as a sold-state storage device (e.g., a solid-state drive, secure digital (SD) card, Flash, Memory Stick, Micro-SD, or other solid-state medium), a magnetic storage device (e.g., a hard disk drive, floppy disk, tape drive, or other magnetic medium), an optical storage device (e.g., CD-ROM, DVD, or other optical medium), or any other suitable storage medium. The sensor data stored by the MCU 720 may include the raw (unprocessed) sensor data, the tagged sensor data, and/or the modulated sensor data.

When the MCU 720 has formatted the sensor data, the MCU 720 then provides the formatted sensor data to the transceiver 730A for broadcasting to the diagnostic system 702. The transceiver 730A may utilize any suitable wireless communication protocol to broadcast the sensor data to the diagnostic system 702 including Bluetooth, IEEE 802.11 (Wi-Fi), wireless UART, cellular telecommunications protocols, etc. In order to facilitate the wireless broadcast, the transceiver 730A may be coupled to a suitable antenna 734. The wireless broadcast is received by a second transceiver 730B coupled to the diagnostic system 702. The second transceiver 730B receives the wireless broadcast, extracts the sensor data from it, and provides the sensor data to the diagnostic system 702.

In many embodiments, the second transceiver 730B provides the sensor data to the diagnostic system 702 in a digital format according to a digital protocol. However, the digital protocol used between the second transceiver 730B and the diagnostic system 702 may be entirely independent of the digital protocols used by the digital sensors 704-718, for example. In this way, the wireless sensing system 700 provides a layer of abstraction that hides the complexity of interfacing with the digital sensors 704-718 and the analog sensors 724 and 726. In other words, application designers writing code for the diagnostic system 702 may safely ignore the particulars of the sensor interface ports 722.

The wireless sensing system 700 supports bidirectional communication between the diagnostic system 702 and the MCU 720. Similar to diagnostic device 201 of FIG. 3, the diagnostic system 702 may use the sensor data to analyze various fabrication conditions and to take corrective action. For example, the diagnostic system 702 may request additional data from a particular sensor, may change a mode of operation of a particular sensor, and may make changes to the operation of a fabrication tool. In particular, the diagnostic system 702 may change the operation of the tool from which the sensor data is obtained as well as any other suitable fabrication tool. To take these actions or others, the diagnostic system 702 provides an instruction to the second transceiver 730B, which then wirelessly provides the instruction to the first transceiver 730A. The MCU 720 receives the instruction via the first transceiver 730A and performs an associated action. In some embodiments, the MCU includes a dedicated control channel 734 for adjusting operation of a fabrication tool according to the instructions of the diagnostic system 702.

Figure 8:
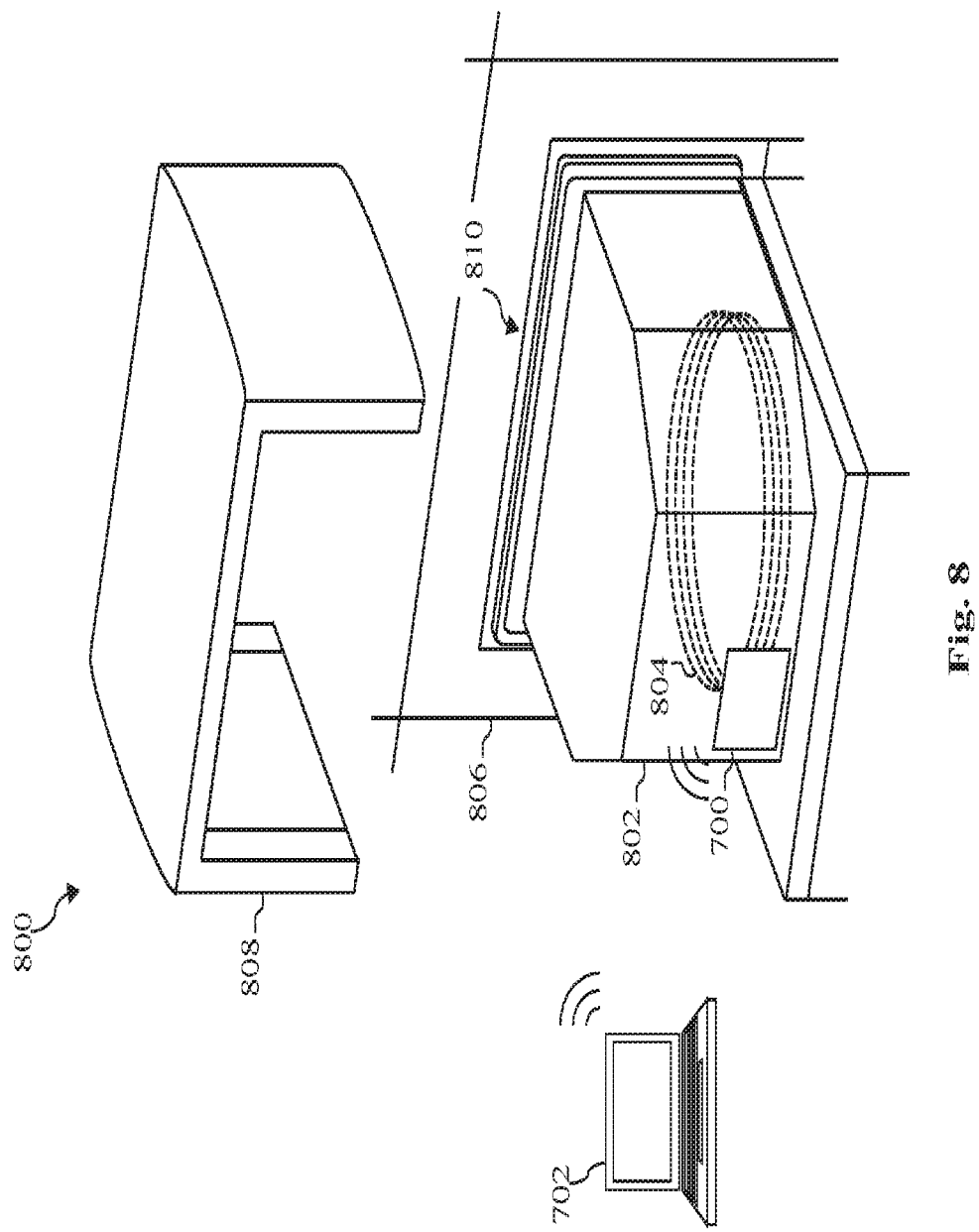
FIG. 8 is a diagrammatic view of a diagnostic wafer handling system according to aspects of the present disclosure.

In addition to those of FIGS. 1, 2, 4, 5A, and 6, another suitable application of the wireless sensing system 700 is described in FIG. 8. FIG. 8 is a diagrammatic view of a diagnostic wafer handling system 800 according to aspects of the present disclosure. The system 800 includes a wireless sensing system 700 coupled to a FOUP 802. The FOUP 802 is merely one example of a wafer transport device used to move semiconductor wafers 804 between fabrication tools such as the illustrated tool 806. Because the FOUP 802 is frequently in motion, the wireless sensing system's 700 lack of wires presents a distinct advantage over conventional wired interfaces. In addition to safely conveying the wafers 804, the FOUP 802 provides a sealed chamber that maintains an ultra-clean environment surrounding the wafers 804, and therefore sensors for monitoring abrupt motion as well as monitoring the sealed environment may be useful. Accordingly, in various embodiments, the wireless sensing system 700 includes the gyroscope 704, the vibration sensor 706, the orientation sensor 708, the leveling sensor 710, the humidity sensor 712, the temperature sensor 714, the CCD sensor 716, and/or the light sensor 718 of FIG. 7. The individual elements of the wireless sensing system 700 shown in FIG. 7 are omitted in FIG. 8 for clarity.

Similar to the vibration sensors describe above, the vibration sensor 706 measures force on the FOUP 802 and may be used by the diagnostic system 702 to detect vibrations and shocks during transport of the FOUP 802. The vibration sensor 706 may include an accelerometer or other motion sensing apparatus to measure the force experienced by the FOUP 802. The gyroscope 704, the orientation sensor 708, and the leveling sensor 710 each measure an orientation of the FOUP 802. Proper orientation and alignment are important when the FOUP 802 is in the grip of the Automated Material Handling System (AMHS) 808 as well as when the FOUP 802 is attached to a loading port 722 of the fabrication tool 806. In fact, a FOUP 802 that is misaligned with the loading port 722 may fail to open or may cause a gap that exposes the wafers 804 or the tool 806 to the cleanroom atmosphere. Thus, the sensor data from the gyroscope 704, the orientation sensor 708, and/or the leveling sensor 710 may be used by the diagnostic system 702 to assess the transport and the docking of the FOUP 802.

The CCD image sensor 716 captures an image from the FOUP's perspective, which may be used by the diagnostic system 702 to assess the docking of the FOUP 802. This may be especially valuable when the FOUP 802 is located in an area where a technician cannot go. Because there are numerous reasons why a FOUP 802 fails to dock or fails to open (e.g., a warped door, a bad seal, etc.) an image is often extremely helpful in diagnosing a problem with the FOUP 802 or the fabrication tool 806.

The temperature sensor 714 and the humidity sensor 712 may be used to monitor the environment within the FOUP. With respect to the humidity sensor 712, in many exemplary fabrication processes, liquid solutions are used to process the wafers 804. Despite even the most exacting drying processes, liquid residues may remain on a wafer after processing. To prevent the residue from contaminating other wafers, an inert gas (often nitrogen) may be used to purge residue vapors and to reduce further outgassing. High humidity may indicate that the nitrogen purging charge was insufficient or that too much time has elapsed between charges. Thus, the humidity sensor 712 measures the humidity within the FOUP 802 and may cause the diagnostic system 702 to request another nitrogen charge.

The final exemplary sensor is a light sensor 718 that may be sensitive to one or more specific wavelengths of light. In contrast to the CCD image sensor 716, the light sensor may measure the amount of light present rather than capturing an image. In many embodiments, available light sensors 718 are more sensitive than available CCD image sensors 716 and are capable of detecting light at lower intensity levels. The light measurement data obtained from the light sensor 718 can be used to detect imperfect seals that allow light to penetrate and/or escape. It is understood that these sensors are merely exemplary, and that the wireless sensing system 700 may include any combination of these sensors (including none) in combination with any other suitable sensors.

The wireless sensing system 700 obtains sensor data from the aforementioned sensors. In some embodiments, this includes transmitting the sensor data from the sensors to the MCU 720 of the wireless sensing system 700. As the respective sensors may be digital, analog, or some combination thereof, obtaining the sensor data may include a digital and/or analog transmission of the data to the MCU 720. Once the data is received, the MCU 720 may perform signal processing to improve the data, may modulate the data for wireless transmission, may tag the data with a sensor ID, and/or may store the data on a storage device 732. The MCU 720 then forwards the data to the transceiver 730A for wireless broadcast to the diagnostic system 702. Based on the sensor data, the diagnostic system 702 may alter the behavior of the sensors or the fabrication tool 806 by broadcasting a response to the wireless sensing system 700.

Figure 9:
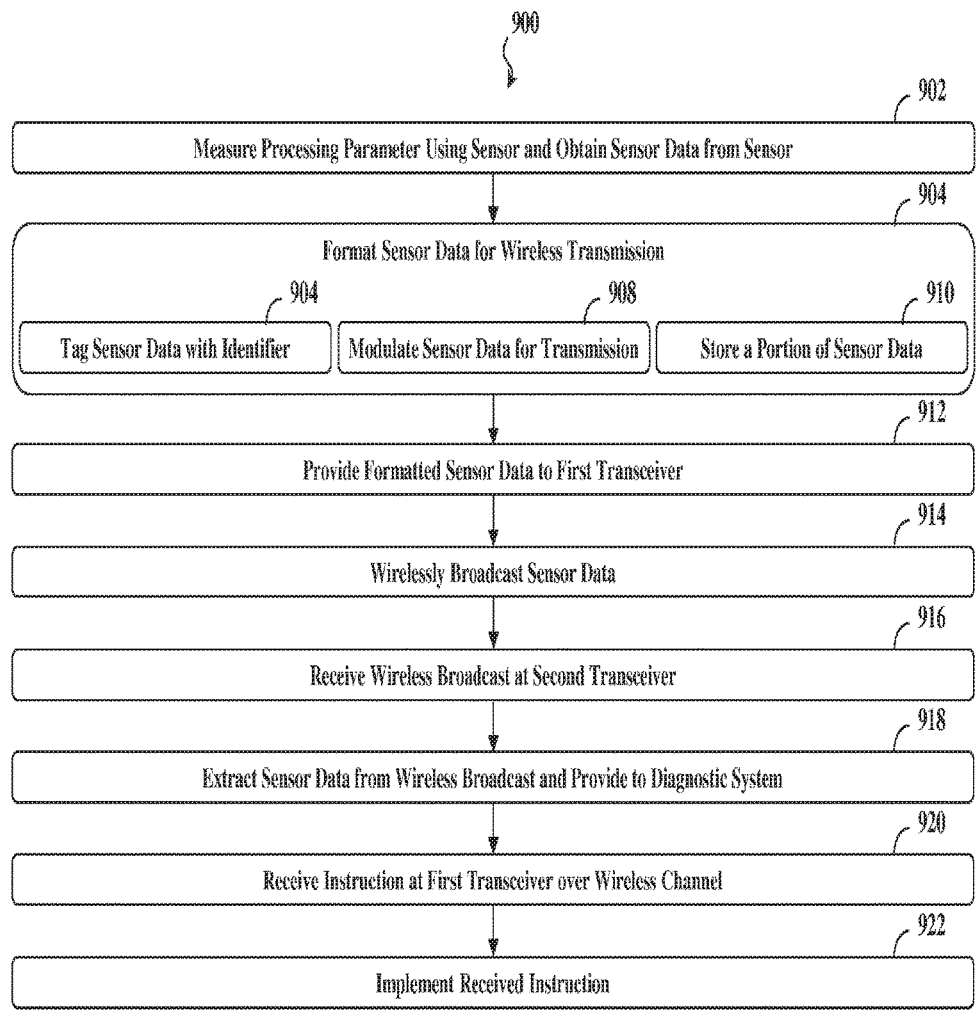
FIG. 9 is a flow diagram of a method of obtaining sensor data according to aspects of the present disclosure.

A method of utilizing the wireless sensing system 700 to obtain sensor data is described in the context of FIG. 9. FIG. 9 is a flow diagram of the method 900 of obtaining sensor data according to aspects of the present disclosure. It is understood that additional steps can be provided before, during, and after the steps of method 900, and that some of the steps described can be replaced or eliminated for other embodiments of the method.

Referring to block 902, a sensor is used to measure a processing parameter and produce corresponding sensor data. In many embodiments, the processing parameter is an aspect of a fabrication process for forming a circuit device on a semiconductor wafer. A wide range of possible sensors are contemplated and provided for, and the techniques for obtaining the sensor data from the sensor may be adapted to the particular sensor. For example, in some embodiments, the sensor reports data in a digital format according to a digital protocol, such as UART, TCP/IP, USB, I²C, and/or other exemplary protocols. In such embodiments, an interface port 722 of a MCU 720 obtains data from the sensor via the corresponding digital protocol. In embodiments where the interface port 722 supports more than one digital protocol, the port 722 may detect the protocol or protocols that both the sensor and the port 722 support. In order to obtain the data, the port 722 may transmit data requests, data acknowledgements, sensor configuration commands, and/or other signals as laid out in the digital protocol.

As a port 722 may be communicatively coupled to more than one sensor, the port 722 may obtain data from the coupled sensors simultaneously or concurrently according to the respective protocols. In one exemplary embodiment, the port 722 uses time-division multiplexing to communicate with two sensors having different and incompatible protocols. During a first time window or interval, the port 722 obtains sensing data from the first sensor using that sensor's protocol. During a subsequent time window, the port 722 obtains sensing data from the second sensor using that sensor's protocol.

Referring to block 904, the MCU 720 formats the sensor data for transmission. As represented by block 906, formatting may include tagging the sensor data with an identifier corresponding to the sensor that produced it. As represented by block 908, formatting may include modulating the sensor data according to a modulation scheme configured for wireless transmission. As discussed above, suitable modulation schemes include quadrature phase shift keying (QPSK), quadrature amplitude modulation (QAM), Gaussian frequency shift keying (GFSK), and/or orthogonal frequency division multiplexing (OFDM). As represented by block 910, formatting may include storing a portion of the data to a storage device 732 coupled to the MCU 720.

Referring to block 912, the MCU 720 provides the formatted sensor data to a first transceiver 730A for wireless transmission. Referring to block 914, the first transceiver 730A wirelessly broadcasts the sensor data. The transceiver 730A may utilize any wireless communication protocol to broadcast the sensor data to the diagnostic system 702 including Bluetooth, IEEE 802.11 (Wi-Fi), wireless UART, and/or cellular telecommunications protocols. The wireless broadcast containing the sensor data is received by a second transceiver 730B in block 916.

Referring to block 918, the second transceiver 730B extracts the sensor data from the wireless broadcast and provides it to a diagnostic system 702 according to a digital protocol. The digital protocol used between the second transceiver 730B and the diagnostic system 702 may be entirely independent of the digital protocols used to obtain sensor data from the sensors. For example, in an embodiment, a port 722 of the MCU 720 obtains sensor data according to a UART protocol, while the second transceiver 730B communicates with the diagnostic system 702 according to the USB protocol.

As described above, the wireless sensing system 700 may also receive instructions and commands from a system such as the diagnostic system 702. Referring to block 920, the first transceiver 730A receives a wireless broadcast containing an instruction from a computing system. The instruction may be directed to changing the behavior of the wireless sensing system 700 or an associated fabrication tool 806. For example, the instruction may request additional data from a sensor, may change a mode of operation of a sensor, or may make changes to the operation of the fabrication tool 806. The instruction may be a response to a previous signal sent by the first transceiver 730A such as the broadcast containing the sensor data. Referring to block 922, the MCU 720 implements the received instruction.

Accordingly, one of the broader forms of the present disclosure involves an apparatus for fabricating a semiconductor device. The apparatus includes a microcontroller having a port coupled to a sensor and a wireless transceiver coupled to the microcontroller. The interface port is operable to obtain sensor data from the sensor according to a digital protocol, and the micro-controller is operable to modulate the sensor data for wireless transmission. The wireless transceiver is operable to receive the modulated sensor data from the microcontroller, wirelessly communicate the modulated sensor data to a computing system, and wirelessly receive a command to adjust operation of at least one of the sensor and an associated fabrication tool. In some such embodiments, the interface port is operable to obtain first sensing data from a first sensor according to a first digital protocol and to obtain second sensing data from the second sensor according to a second digital protocol that is different from the first digital protocol.

In another of the broader forms of the present disclosure, a semiconductor wafer transport device is provided. The device includes a sealed portion operable to hold a semiconductor wafer, and a wireless sensing system including: a controller communicatively coupled to a sensor via a port of the controller, and a wireless transceiver communicatively coupled to the controller. The controller is operable to obtain sensor data related to the semiconductor wafer transport device from the sensor and to provide the obtained sensor data to the wireless transceiver. The wireless transceiver is operable to wirelessly communicate the sensor data to a diagnostic system.

In yet another of the broader forms, a method of obtaining data is provided. The method includes communicating with a sensor according to a first digital protocol to obtain data from the sensor, formatting the data for wireless transmission, wirelessly providing the formatted data from a first transceiver to a second transceiver, and providing the formatted data from the second transceiver to a computing system according to a second digital protocol that is independent of the first digital protocol. In some such embodiments, the formatting of the data for wireless transmission includes tagging the data obtained from the sensor with an identifier of the sensor.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:
1. An apparatus comprising:
 a microcontroller communicatively coupled to a first sensor and a second sensor, wherein the first sensor and the second sensor monitor different parameters, and further wherein the microcontroller is configured to:

receive first sensor data in digital form from the first sensor and receive second sensor data in digital form from the second sensor, the first sensor data and the second sensor data corresponding with the different parameters, and modulate the first sensor data and the second sensor data for wireless transmission; and a wireless transceiver communicatively coupled to the microcontroller, wherein the wireless transceiver is configured to:

receive the modulated first sensor data and the modulated second sensor data from the microcontroller, wireles sly communicate the modulated first sensor data and the modulated second sensor data in digital form to a computing system, and wirelessly receive a command to adjust operation of at least one of the first sensor, the second sensor, or an associated fabrication tool.

2. The apparatus of claim 1, further comprising an analog-to-digital converter configured to receive third sensor data in analog form from a third sensor, wherein:

the microcontroller is further communicatively coupled to the third sensor, the microcontroller is further configured to receive third sensor data in digital form from the analog-to-digital converter and modulate the third sensor data for wireless transmission, wherein the third sensor data corresponds with a different parameter than the first sensor data and the second sensor data, and the wireless transceiver is further configured to receive the modulated third sensor data in digital form from the microcontroller and wireles sly communicate the modulated third sensor data to the computing system.

3. The apparatus of claim 1, wherein the microcontroller obtains the first sensor data and the second sensor data according to a digital protocol that is different than a digital protocol used by the wireless transceiver for wirelessly communicating the modulated first sensor data and the modulated second sensor data.

4. The apparatus of claim 1, wherein the microcontroller includes an interface port communicatively coupled to the first sensor and the second sensor, such that the microcontroller receives the first sensor data in the digital form and the second sensor data in the digital form via the interface port.

5. The apparatus of claim 4, wherein the interface port is configured to obtain data from the first sensor and the second sensor sequentially using time-division multiplexing, such that the interface port requests the first sensor data during a first time interval and the second sensor data during a second time interval.

6. The apparatus of claim 1, wherein the microcontroller obtains the first sensor data from the first sensor according to a first digital protocol and the second sensor data from the second sensor according to a second digital protocol that is different from the first digital protocol.

7. The apparatus of claim 1, wherein the microcontroller includes a controller channel for adjusting operation of at least one of the first sensor, the second sensor, or the associated fabrication tool based on the command received by the wireless transceiver.

8. The apparatus of claim 1, wherein the apparatus is detachably coupled to a front-opening universal pod (FOUP).

9. The apparatus of claim 8, wherein the first sensor and the second sensor are selected from the group consisting of a gyroscope, a vibration sensor, an orientation sensor, a leveling sensor, a humidity sensor, a temperature sensor, a CCD, and a light sensor.

10. A semiconductor wafer transport device comprising:

a sealed portion configured to hold a semiconductor wafer; and a wireless sensing system including:

a microcontroller that includes a multi-protocol interface port, wherein the multi-protocol interface port is communicatively coupled to a first sensor and a second sensor, wherein the first sensor is configured to monitor a first parameter associated with transporting the semiconductor wafer and the second sensor is configured to monitor a second parameter associated with transporting the semiconductor wafer, the first parameter being different than the second parameter, and a wireless transceiver communicatively coupled to the microcontroller, wherein the multi-protocol interface port is configured to receive first sensor data associated with the first parameter in digital form according to a first digital protocol from the first sensor and second sensor data associated with the second parameter in digital form according to a second digital protocol from the second sensor, the second digital protocol being different than the first digital protocol, and further wherein the microcontroller is configured to transmit the received first sensor data and the received second sensor data to the wireless transceiver, and wherein the wireless transceiver is configured to wirelessly communicate the first sensor data and the second sensor data to a diagnostic system.

11. The semiconductor wafer transport device of claim 10, wherein:

the multi-protocol interface port is a first interface port;

the wireless sensing system further includes an analog-to-digital converter;

the microcontroller further includes a second interface port that is communicatively coupled to an analog-to-digital converter and a third sensor configured to monitor a third parameter associated with transporting the semiconductor wafer, the third parameter being different than the first parameter and the second parameter; and wherein the analog-to-digital converter is configured to convert third sensor data associated with the third parameter in analog form to digital form, the second interface port is configured to receive the third sensor data associated with the third parameter in digital form, and the microcontroller is configured to transmit the received third sensor data to the wireless transceiver.

12. The semiconductor wafer transport device of claim 10, wherein the first parameter and the second parameter are selected from the group consisting of: movement of the semiconductor wafer transport device, docking of the semiconductor wafer transport device in a load port of a fabrication tool, and an environment within the sealed portion.

13. The semiconductor wafer transport device of claim 10, wherein the first sensor and the second sensor are selected from the group consisting of a gyroscope, a vibration sensor, an orientation sensor, a leveling sensor, a humidity sensor, a temperature sensor, a CCD, and a light sensor.

14. The semiconductor wafer transport device of claim 10, wherein the wireless transceiver is further configured to receive an instruction to change operation of the first sensor or the second sensor.

15. The semiconductor wafer transport device of claim 10, wherein the the first digital protocol is UART and the second digital protocol is I²C.

16. The semiconductor wafer transport device of claim 10, wherein the multi-protocol interface port is configured to implement a time-division technique, such that the multi-protocol interface port receives the first sensor data from the first sensor during a first time interval and receives the second sensor data from the second sensor during a second time interval, the second time interval being different than the first time interval.

17. A method for wirelessly communicating digital data, the method comprising:
   receiving first sensor data in digital form, by a microcontroller of a wireless sensing system, from a first sensor according to a first digital protocol, wherein the first sensor data corresponds with a first parameter;
   receiving second sensor data in digital form, by the microcontroller of the wireless sensing system, from a second sensor according to a second digital protocol, wherein the second sensor data corresponds with a second parameter that is different than the first parameter;
   formatting, by the microcontroller of the wireless sensing system, the received first sensor data and the received second sensor data for wireless transmission;
   receiving, by a wireless transceiver of the wireless sensing system, the formatted first sensor data and the formatted second sensor data; and
   wirelessly transmitting, by the wireless transceiver the wireless sensing system, the formatted first sensor data and the formatted second sensor data in digital form according to a third digital protocol to a diagnostics system, wherein the third digital protocol is different than the first digital protocol and the second digital protocol.

18. The method of claim 17, the method further comprising:
   receiving third sensor data in analog form, by an analog-to-digital converter of the wireless sensing system, from a third sensor;
   receiving the third sensor data in digital form, by the microcontroller of the wireless sensing system, from the analog-to-digital converter;
   formatting, by the microcontroller of the wireless sensing system, the third sensor data received from the third sensor for wireless transmission; and
   wirelessly transmitting, by the wireless transceiver of the wireless sensing system, the formatted third sensor data in digital form according to the third digital protocol.

19. The method of claim 17, wherein the first sensor data is received by an interface port of the microcontroller during a first time interval and the second sensor data is received during a second time interval by the interface port.

20. The method of claim 17, wherein the first digital protocol is different from and incompatible with the second digital protocol.

* * * * *